United States Patent [19]

Hartzler

[11] 4,231,939
[45] Nov. 4, 1980

[54] 2,5-DIOXO-3H,6H-FURO[(3,2-b]FURAN-3A-6A-DIACETIC ACID AND SALTS THEREOF

[75] Inventor: Harold E. Hartzler, Goshen, Ind.

[73] Assignee: Miles Laboratories, Inc., Elkhart, Ind.

[21] Appl. No.: 97,307

[22] Filed: Nov. 26, 1979

[51] Int. Cl.³ .......................................... C07D 307/93
[52] U.S. Cl. ............................... 260/343.6; 260/339; 260/429 J; 260/435 R; 260/438.1; 260/439 CY; 562/582
[58] Field of Search ...................................... 260/343.6

[56] References Cited
U.S. PATENT DOCUMENTS

| | | | |
|---|---|---|---|
| 4,032,651 | 6/1977 | Aldridge et al. | 260/343.6 |
| 4,103,023 | 7/1978 | Aldridge et al. | 260/343.6 |

Primary Examiner—Ethel G. Love
Attorney, Agent, or Firm—Jerome L. Jeffers

[57] ABSTRACT

Disclosed is the title compound having the structural formula:

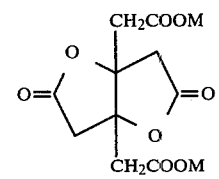

This compound in which M is hydrogen, an alkali metal or ammonium, has utility as a chelating agent which exhibits stability constants with various metal ions which are intermediate between those of EDTA and citric acid.

5 Claims, No Drawings

2,5-DIOXO-3H,6H-FURO[3,2-b]FURAN-3A,6A-DIACETIC ACID AND SALTS THEREOF

BACKGROUND OF THE INVENTION

A chelating agent is a compound containing donor atoms that can combine by coordinate bonding with a single metal ion to form a cyclic structure called a chelation complex or, simply, a chelate. Because the donor atoms are connected intramolecularly by chains of other atoms, a chelate ring is formed for each donor atom after the first which coordinates with the metal. Each ring gives the appearance of a metal atom being held in a pincer formed by other atoms. The technological importance of chelation is based on the almost universal presence of metal ions of one kind or another. They are present either naturally or, in certain instances by intentional addition. Chelating agents provide a means of manipulating and controlling metal ions by forming complexes that usually have properties that are markedly different from those of the original ions or the chelants. These properties may serve to reduce undesirable effects of metal ions as in sequestration, or to create desirable effects as in metal buffering and solubilization.

The structural essentials of a chelate are coordinate bonds between a metal ion and two or more atoms in the molecule of the chelating agent. The coordinating atoms of the chelating agent are electron donors and the metal ion is an electron acceptor. When coordinate bond formation occurs between the metal and two donor atoms, the atoms of the ligand that connect the donor atoms complete the ring that gives the structure its chelate character.

Commerically useful chelating agents include ethylene-diamine tetraacetic acid (EDTA) and citric acid. Other compounds known to be useful as chelating agents include ethylenediamine-N,N'-diacetic acid, alanine-N,N'-diacetic acid, anthranil-N,N'-diacetic acid and 1,2-dihydroxyanthraquinone-3-methylamine-N,N'-diacetic acid.

SUMMARY OF THE INVENTION

The present invention involves 2,5-dioxo-3H,6H-furo[3,2-b]furan-3a6a-diacetic acid and salts thereof corresponding to the formula:

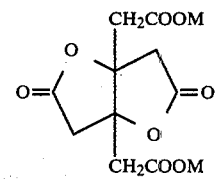

where M is hydrogen, an alkali metal or ammonium.

The diacetic acid is prepared by treating 9,10-dihydroxy-1,4,5,8-tetrahydronaphthalene with ozone and hydrogen peroxide.

DETAILED DESCRIPTION

The novel compound disclosed herein can be prepared by the action of ozone and hydrogen peroxide on 9,10-dihydroxy-1,4,5,8-tetrahydronaphtalene, a known compound, as indicated by the following equation:

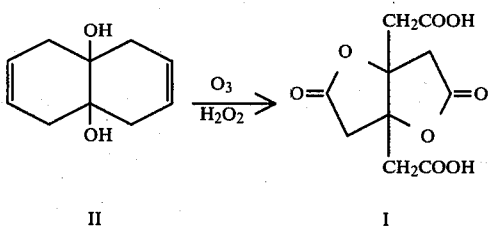

While the invention is not intended to be limited to any particular theory, it is believed that the foregoing reaction proceeds as follows:

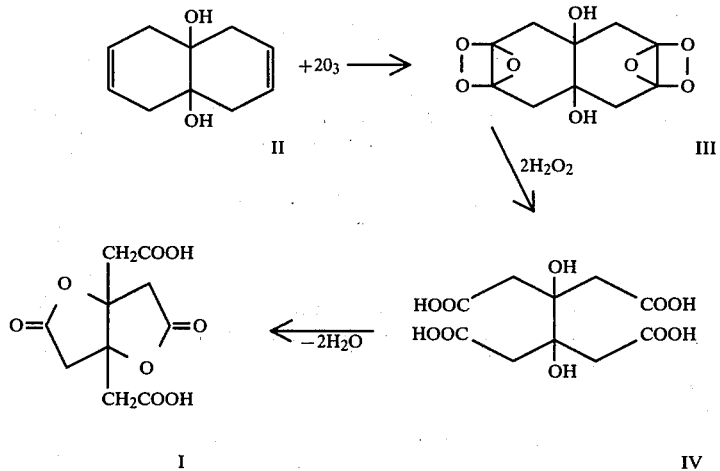

The reaction can be carried out in any suitable solvent, i.e., those solvents which do not react with ether the reactants or the products.

The preparation of Compound I is further illustrated by the following example.

EXAMPLE I

Preparation of 2,5-Dioxo-3H,6H furo[3,2-b]furan 3a6a diacetic acid

Compound II, 9,10-dihydroxy-1,4,5,8-tetrahydronaphthalene (5 g, 0.03 mole), in 100 ml of dichloromethane was stirred at about −50° C. while a stream of ozone in oxygen was bubbled into the mixture. After about 30 minutes the solution turned blue indicating the presence of excess ozone. The solution was warmed to 0° C. whereupon 50 ml of 88% formic acid and 25 ml of 30% hydrogen peroxide were added. At this point the dichloromethane was blown off in a stream of nitrogen while the mixture was warmed to 40° C. After 1 hour at 40° the temperature was raised to 65° C. and held for 1 hour and was then treated with a small amount of 10% platinum on carbon catalyst to decompose the remaining peroxides. The catalyst was filtered and the filtrate concentrated to dryness on a rotary evaporator. The white solid which remained was boiled up in 2-propanol, cooled and dried in air to yield a product which melted at 240° C. with effervescence.

Analysis: Calculated for $C_{10}H_{10}O_8$: C, 46.51; H, 3.91. Found: C, 46.47; H, 3.94.

This material showed strong absorptions at 1720 cm$^{-1}$ and 1790 cm$^{-1}$ in the IR indicative of carboxyl carbonyl and lactone carbonyl, respectively. The NMR showed singlets at 3.05 ppm (4H), 3.18 ppm (2H) and 3.33 ppm (2H). A very broad absorption centered at 11.7 ppm integrates for 2H. This material fragmented too badly to gain any structural information in the mass spectrometer.

A sample of the above material was treated with ethereal diazomethane giving a yellow oil which was dried under high vacuum to yield the methyl ester of Compound I for identification by mass spectral analysis.

Analysis: Calculated for $C_{12}H_{14}O_8$: C, 50.35; H, 4.93 Found: C, 50.60, H, 5.12.

The mass spec of this material showed a parent ion peak (mass 286).

All the above information confirms the structure as being that of the title compound.

The compound is normally used in the form of its alkali metal or ammonium salt due to the increased water solubility of the salts as compared to the free acid.

EXAMPLE II

Stability Constants of Metals with 2,5-Dioxo-3H,6H furo[3,2-b]furan 3a6a-diacetic acid (lactone)

The procedure for determining stability constants for (lactone) with various metals by the method of R. W. Schmid and C. N. Reilly, JACS 78, 5513 (1956) was used.

The cell consisted of a 50 ml beaker, a glass electrode, a J-tube mercury electrode and a saturated calomel electrode. About 30 ml of the solution was taken for measurement and stirred by means of a magnetic stirrer. The pH was varied by dropwise addition of sodium hydroxide or perchloric acid. The pH was measured with a Corning Model 125 pH meter and the potential by the same Corning Model 125 meter. Equilibrium within ±1 mμ generally was reached in one minute.

100 ml solutions were made up to contain 0.1 molar $NaClO_4$, 0.0001 moles $HgCl_2$, 0.0007 molar lactone and 0.001 moles of the metal to be tested.

TABLE I

| Metal | Experimental data: Constant voltage with varying pH |
|---|---|
| Cu++ | .247 volts |
| Mg++ | .308 volts |
| Fe++ | .245 volts |
| Cd++ | .260 volts |
| Zn++ | .255 volts |
| CO++ | .264 volts |
| Mn++ | — |
| Ni++ | — |

TABLE I-continued

| Metal | Experimental data: Constant voltage with varying pH |
|---|---|
| Pb++ | — |

The stability constant Log $K_{MeLac}$ can be calculated from the equation ①.

$$E \text{ measured} = E^a{}_{Hg} + 0.0296 \log \frac{[C_{me}][C_{HgLac}]}{[C_{MeLac}]K_{HgLac}} + 0.0296 \log K_{MeLac} \quad ①$$

In this equation $K_{HgLac}$ is unknown, however a close approximation can be determined by comparing the potential of Hg EDtA solution and Hg Lac solution at the same concentration ϵ pH. At Ph 4 the following data was obtained

| E measured Hg EDtA | .200 |
|---|---|
| E measured Hg Lac | .318 |
| K Hg EDtA from Lit. | 22.1 |

Therefore $$K_{HgLac} = 22.1$$

$$\frac{.6105 - .318}{.0296} \qquad \frac{.6105 - .200}{.0296}$$

$$K_{HgLac} = 15.7$$

Using this value in equation 1 it reduces to the following $$E \text{ measured} = 0.6105 + 0.0296 \log \frac{4 \times 10 - 4 \times 1 \times 10 - 4}{6 \times 10 - 6} -$$
$$0.0296 \times 15.7 + 0.0296 \log K_{MeLac}$$

$$\log K_{MeLac} = \frac{-0.6105 - E \text{ measured}}{0.0296} + 4.18 - 15.7$$

$$\log K_{MeLac} = 19.88 - \frac{0.6105 - E \text{ measured}}{0.0296}$$

Using the data from Table 1 the following values are obtained

TABLE II

| Metal | Lactone | EDtA[1] | Citric Acid[2] |
|---|---|---|---|
| Hg++ | 15.7 | 22.1 | 11.1 |
| Cd++ | 8.0 | 16.4 | 3.1 |
| Mg++ | 9.6 | 8.9 | — |
| Cs++ | 7.6 | 10.7 | 3.9 |
| Fe++ | 7.6 | — | 3.0 |
| Cu++ | 7.6 | 18.7 | 7.3 |
| Zn++ | 7.9 | 16.4 | 5.5 |
| Pb++ | — | 17.9 | 5.7 |
| Mn++ | — | 13.8 | 5.6 |
| Co++ | 7.8 | — | — |
| Ni++ | — | — | — |

[1] From Schmid and Reilly JACS 78, (1956)
[2] By above method

From Table II it can be determined that the stability constants of various metal ions with the compound of the present invention are intermediate between those of EDTA and citric acid indicating utility as a chelating agent.

What is claimed is:
1. 2,5-dioxo-3H,6H,furo[3,2-b]furan-3a,6a-diacetic acid and salts thereof characterized by the structural formula

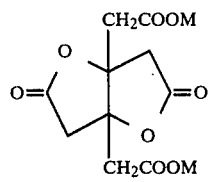

wherein M is hydrogen, an alkali metal or ammonium.

2. A compound as defined by claim 1 wherein M is hydrogen.

3. A compound as defined by claim 1 wherein M is an alkali metal.

4. A compound as defined by claim 1 wherein M is ammonium.

5. A method for the preparation of 2,5-dioxo-3H,6H-furo[3,2-b]furan-3a,6a-diacetic acid which comprises oxidizing 9,10-dihydroxy-1,4,5,8-tetrahydronaphthalene with ozone and hydrogen peroxide for a time sufficient to form the desired product.

* * * * *